United States Patent [19]

Neeman et al.

[11] 4,370,413

[45] Jan. 25, 1983

[54] MICROMETHOD FOR THE DETERMINATION OF ENDOTOXINS

[75] Inventors: Ishak Neeman, Haifa, Israel; Stephen L. Gaffin, Durban, South Africa

[73] Assignee: Technion Research and Development Foundation, Ltd., Haifa, Israel

[21] Appl. No.: 235,153

[22] Filed: Feb. 17, 1981

[30] Foreign Application Priority Data

Feb. 14, 1980 [IL] Israel .......................................... 59383

[51] Int. Cl.$^3$ .......................... C12Q 1/06; C12Q 1/29; C12Q 1/04; C12M 1/34
[52] U.S. Cl. ........................................ 435/39; 422/61; 435/29; 435/34; 435/291; 435/807; 435/810; 436/502
[58] Field of Search ................. 435/7, 29, 34, 39, 287, 435/291; 23/230 B; 422/61

[56] References Cited

U.S. PATENT DOCUMENTS

| | | | |
|---|---|---|---|
| 3,915,805 | 10/1975 | Levin | 435/34 X |
| 4,038,029 | 7/1977 | Teller et al. | 435/7 X |
| 4,067,776 | 1/1978 | Khan | 435/34 |
| 4,096,091 | 6/1978 | Hopkins | 435/7 X |
| 4,104,030 | 8/1978 | Hopkins et al. | 435/34 X |

*Primary Examiner*—Robert J. Warden
*Attorney, Agent, or Firm*—Browdy and Neimark

[57] ABSTRACT

An improved micromethod for the quantitative determination of endotoxins with Limulus Amebocyte Lysate (L.A.L.) reagent is based on the discovery that if L.A.L. reagent and a sample containing microquantities of endotoxin are incubated in a capillary tube, a clot will be formed in the plug preventing any outflow of liquids when low hydrostatic pressure is applied. Increasing the pressure will eventually force out the clot plugging the capillary and the liquid will suddenly erupt giving a clear yes-no indication of the presence of endotoxin. The hydrostatic pressure indicated to cause this eruption is a relatively precise indication of the extent of clotting which, in turn, is indicative of the concentration of endotoxin in the liquid. A kit which can be used to perform this test is also disclosed.

8 Claims, 1 Drawing Figure

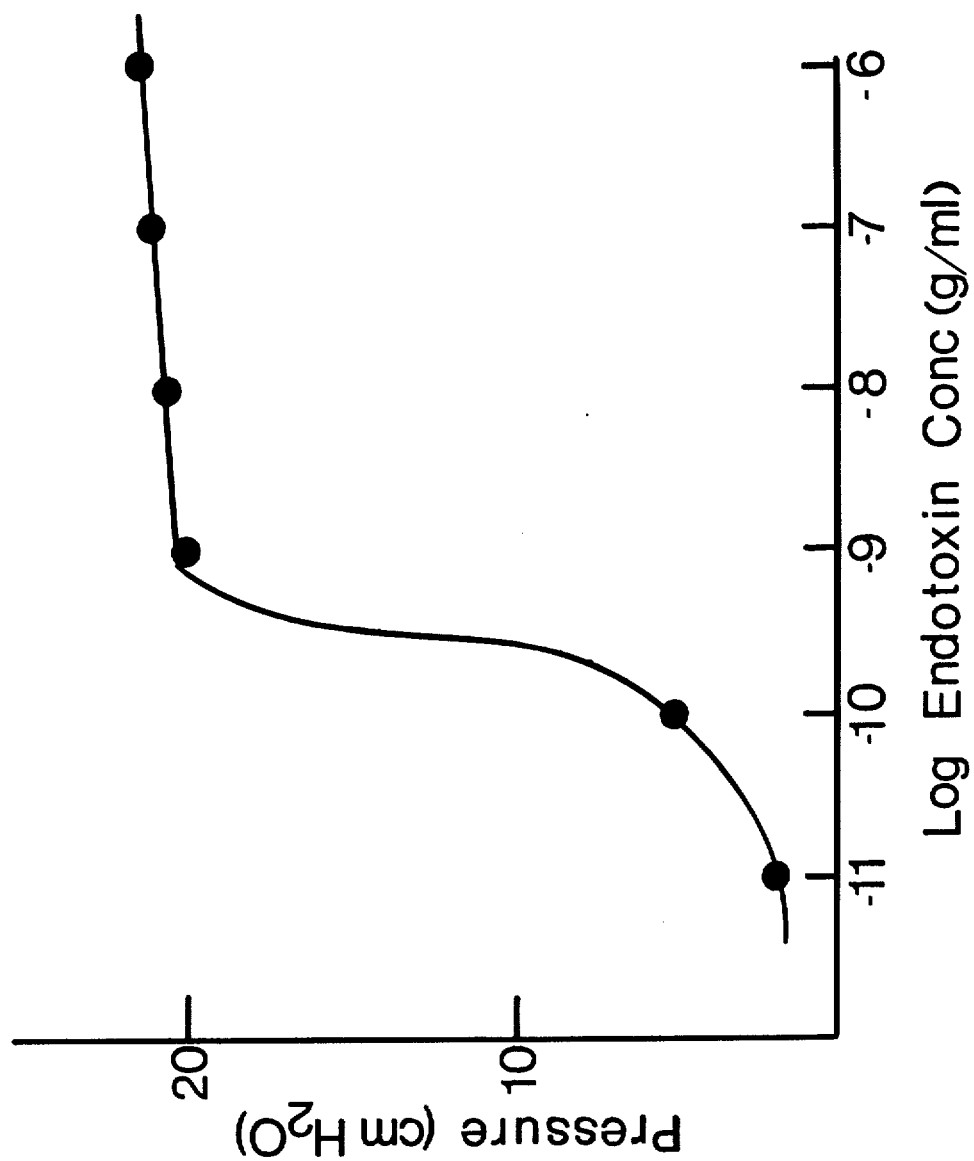

MICROMETHOD FOR THE DETERMINATION OF ENDOTOXINS

The present invention relates to a new method for the determination of bacterial toxins, so called endotoxins. More particularly the invention relates to a new method for the determination of endotoxins by using Limulus Amebocyte Lysate (L.A.L.) assay.

L.A.L. is a well-known reagent prepared from the circulating blood cells (amebocytes) of the horseshoe crab (Limulus polyphemus). It has already been found that L.A.L. should be considered as a sensitive indicator for the presence of bacterial endotoxins. The use of L.A.L. in testing many biological products and devices has been demonstrated to be simpler, more rapid, more sensitive and usually more accurate than the results obtained on the same sample with the rabbit pyrogen test. In addition to that, the L.A.L. assay is more economical and requires a smaller volume of sample for testing, than the rabbit test. Today the L.A.L. assay has successfully replaced in many laboratories the standard rabbit pyrogen test for determining endotoxins.

The known L.A.L. assay is based upon the fact that the addition of a solution containing endotoxins to a suitable L.A.L. preparation and subsequent incubation at 37° C., causes the formation of a solid gel or an increase in viscosity and/or turbidity of the mass. Although the assay is very simple to be carried out, it suffers from several disadvantages which discourage its more widespread use:

(a) The test requires the use of 100 microliters of L.A.L. reagent, which is considered a very expensive reagent.

(b) The test is too subjective in determining the end point of the reaction concerning the appearance of a solid gel, loose gel, increase in viscosity, etc.

(c) The test is practically only qualitative.

Research work on L.A.L. assay was carried out in the last years to obviate the above drawbacks and some improvements are reported. Thus a micromethod slide test was described in *J. Pharm. Sci.*, 63, pages 808-809, as a modified L.A.L. assay. The micromethod consists in placing only 10 microliters of Limulus reagent on the surface a slide (e.g. a glass plate with a black backside) using a calibrated glass capillary tube. After addition of 10 microliters of the sample to the reagent on the slide and mixed with the capillary tube, the slide is introduced into a moist chamber and the whole assembly is incubated at 37° C. A solid gel or increase in viscosity is easily detected. Although this method requires less reagent than the standard L.A.L. assay, it is still considered a subjective test and again is not quantitative.

Other approaches for the L.A.L. assay are based on the turbidity effect involving a high dilution and its determination by spectrophotometer, or inducing a Brownian motion and its determination by the use of microscope.

It is an object of the present invention to provide a simple method for the determination of endotoxins by the L.A.L. assay. It is another object of the present invention to provide a simple and inexpensive method for the determination of endotoxins by L.A.L. assay on a micro scale. It is yet another object of the present invention to provide a simple micromethod for the determination of endotoxins by L.A.L. assay which is objective, quantitative and without loss of sensitivity. Thus the invention consists in a micromethod for the determination of endotoxins with Limulus Amebocyte Lysate (L.A.L.) reagent, which comprises the steps of: (a) admixing the sample containing the endotoxins with a microamount of L.A.L. reagent; (b) introducing the mixture into a capillary tube; (c) incubating the capillary tube at a temperature in the range of 20° C. to 40° C. and (d) measuring the hydrostatic pressure required to cause the formed viscous mass to flow from said capillary tube. The invention is based on the discovery that in a mixture of L.A.L. reagent with the endotoxin after incubation at a temperature in the range of 20° to 40° C., there is a sharp increase in the hydrostatic pressure required to cause the viscous mass to flow from a capillary tube, when the endotoxin is present at concentration of $1 \times 10^{-9}$ g/ml and above depending on the sensitivity of the L.A.L.

In the attached FIG. 1, there is presented a graph which correlates the hydrostatic pressure (expressed in cm of $H_2O$) required to cause the Limulus amebocyte Lysate-test solution to flow from a 10 microliter capillary pipet, as a function of log endotoxin concentration expressed in g/ml. Each point is the mean of a representative experiment of five determinations. The L.A.L. test solution consisted of equal volumes of L.A.L. reagent and test solution, incubated for 60 minutes at 37° C. It has been found that the increase in the required hydrostatic pressure, occured at the same endotoxin concentration which causes gelation of the sample in the standard L.A.L. assay. In the latter case the gel could withstand 180° inversion at endotoxin concentrations $1 \times 10^{-9}$ g/ml or above depending on the L.A.L. and thus no loss in sensitivity occured with the microassay according to the present invention.

The incubation is carried out at a temperature in the range of 20° to 40° C. and preferably between 30° C. and 40° C. The time for said incubation is generally between 10 minutes and 60 minutes.

The endotoxin determination according to the present invention is very simple to be carried out, rapid and correlates well with the results of the standard L.A.L. assay procedure. Moreover at $1 \times 10^{-10}$ g/ml endotoxin, some subjectively evaluated increase in viscosity and turbidity was observed in the standard method even though no solid gel was formed, while at the same endotoxin concentration the pressure required to cause the gel to flow from the capillary increased from 2.2 cm $H_2O$ to 5.0 cm $H_2O$, which is a quantifiable and reproducible value.

In the last years, and particularly after 1977 when the L.A.L. assay was recognized as an alternative test for the rabbit pyrogen test (Randolph W., Federal Register 42, 57749-50), the use of L.A.L. assay has greatly increased in the pharmaceutical industry, hospital laboratories, nuclear medicine, food industry, sewage water, drinking water, etc., for the rapid detection of the presence of endotoxins in the various substances. It can now also be used to detect endotoxin in human plasma, after the recent development of a reliable method for inactivating a L.A.L. clot inhibitor present in plasma. The micromethod according to the present invention can also be used for in-house product testing of large volumes of parenteral solutions prior to their undergoing the standard rabbit pyrogen test.

In addition to the fact that the method according to the present invention has an objective character, it can be quantifiable obtaining accurate and reproducible results. When concentrations higher than $10^{-8}$ g/ml are present, the solution can be diluted thus obtaining a more distinct slope than that which appeared in the graph of FIG. 1.

One of the advantages of the present invention is the fact that the new method of endotoxin determination, does not require sophisticated and expensive equipment. The determination of the hydrostatic pressure required to cause the flow of the viscous L.A.L.-sample can be carried out by using any known device for this matter. A person skilled in the art after reading the present specification could provide various devices for this determination. Thus, for instance, one approach envisaged would be an elevated fluid-filled reservoir connected through flexible tubing clamped at one end to a capillary filling adapter. A capillary tube containing the L.A.L.-mixture after incubation, would be inserted into the filling adapter and then the capillary will be brought to a height equal to zero hydrostatic pressure and the clamp opened. By slowly lowering the capillary, a hydrostatic pressure will be generated due to the difference in height between the capillary and the top of the reservoir and accordingly the viscous mass will flow outward. The accuracy of the endotoxin determination can be increased by carrying out a blank calibration of the device, with a solution of 0.9% of sodium chloride (without the L.A.L. reagent) so that the hydrostatic pressure caused by the surface effect of flowing a solution through the capillary, would be taken into account.

It could also be envisaged to use a standard air manometer for the measurement of the hydrostatic pressure.

Another approach for the determination of the hydrostatic pressure, is to use a device similar to a syringe, wherein a prior calibration of the empty reservoir is done in respect to the hydrostatic pressure caused by plunging the piston. The reservoir will be already marked with divisions corresponding to cm $H_2O$ pressure.

While the invention has been illustrated with certain types of devices, it will be understood that it is not intended to limit the invention to these particular embodiments. On the contrary, it is intended to cover all alternatives, modifications and equivalents as may be included within the scope of the invention as defined by the appended claims.

The method according to the present invention requires only a small amount of the expensive L.A.L. reagent, which by itself is of great importance from the economical aspect. But at the same time, the method will also decrease the ecologic pressure on horseshoe crabs which causes drastic reduction in population, due to the often fatal bleeding which is part of the L.A.L. production.

The method can be easily carried out even by an unskilled person and thus it will be indicated to be used in a kit containing already the graph correlating the hydrostatic pressure with the endotoxin determination. The kit will also contain a micro capillary pipet and the device for measuring the flow of viscous mass, obtained after mixing the L.A.L. reagent with the sample to be tested.

The invention will be hereinafter illustrated by the following examples, being understood that these are not limiting the scope of the invention.

EXAMPLE 1

An amount of 10 microliters of a sample of injectable saline solution to be tested was mixed with 10 microliters of L.A.L. reagent in a sterile pyrogen-free tube. 10 microliters of the mixture were placed into a 10 microliter disposable capillary pipet and incubated for one hour at 37° C. The capillary was connected through a capillary filler accessory to a flexible tubing connected to a fluid filled reservoir. The hydrostatic pressure on the capillary is gradually increased by lowering the height of the capillary until the viscous mass suddenly spurts from the capillary and the hydrostatic pressure at this height was recorded as cm $H_2O$. Controls of standard endotoxin solutions show this spurt at 3 cm $H_2O$ for $10^{-10}$ g/ml and 23 cm $H_2O$ for $10^{-9}$ g/ml endotoxin. Therefore the saline for injection had an endotoxin concentration between $10^{-10}$ g/ml and $10^{-9}$ g/ml. A comparative test was carried out using the standard method with L.A.L. reagent. An amount of 0.1 ml of the same injectable saline solution as used above, was mixed with 0.1 ml of L.A.L. reagent in a 12×75 ml sterile pyrogen-free test tube. The test tube was incubated for one hour at 37° C. and then inverted 180°. The solution flowed out of the tube, which indicated that the injectable saline solution had an endotoxin concentration of less than $1 \times 10^{-9}$ g/ml, depending on the sensitivity of the L.A.L. as determined by testing controls of standard endotoxin solutions at the same time.

EXAMPLES 2-5

In a similar manner test solutions of the following substances were carried out:
Aminophylline.
Water for injection.
A calcium solution for injection.
Human plasma.

The results on endotoxin determination correlate very well with the known standard method.

The same accuracy of the results was obtained when the hydrostatic pressure was measured by a standard air manometer.

We claim:

1. A micromethod for the quantitative determination of endotoxins with Limulus Amebocyte Lysate (L.A.L.) reagent, which comprises the steps of: (a) admixing the sample containing the endotoxins with a microamount of L.A.L. reagent; (b) introducing the mixture into a capillary tube; (c) incubating the capillary tube at a temperature range of 20° to 40° C.; (d) measuring the hydrostatic pressure required to cause the formed viscous mass to flow from said capillary tube; and (e) determining the quantity of endotoxin in the sample by comparing the measured hydrostatic pressure to a previously determined standard relating hydrostatic pressure to endotoxin content.

2. A micromethod for the quantitative determination of endotoxins according to claim 1, wherein said incubation is carried out for ten to sixty minutes.

3. A micromethod for the quantitative determination of endotoxins according to claim 1, wherein a dilution of the sample is carried out prior to the measurement of the hydrostatic pressure.

4. A micromethod for the quantitative determination of endotoxins according to claim 1, wherein an elevated fluid-filled reservoir connected through flexible tubing clamped at one end to a capillary filling adapter is used for measuring the hydrostatic pressure.

5. A micromethod for the quantitative determination of endotoxins according to claim 1, wherein a standard air monometer is used for measuring the hydrostatic pressure.

6. A micromethod for the quantitative determination of endotoxins according to claim 1, wherein the sample comprises an injectable saline solution.

7. A kit for carrying out a micromethod for the quantitative determination of endotoxins with Limulus Amebocyte Lysate (L.A.L.) reagent, comprising:

a plurality of capillary size reaction chamber means for receiving a mixture of a sample containing endotoxin and a microamount of L.A.L. reagent, said reaction chamber means comprising capillary tubes;

hydrostatic pressure measuring means for determining the hydrostatic pressure required to cause the endotoxin-L.A.L. reaction product to flow from said capillary tube, said pressure measuring means comprising a watertight vessel having an outlet tube at or near the bottom thereof, said outlet tube including a length of flexible tubing connectable to one of said capillary tubes; and an empirical graph correlating the hydrostatic pressure as measured by said pressure measuring means with the quantitative content of endotoxin in the sample introduced into said reaction chamber means.

8. A kit in accordance with claim 7 and further including a supply of L.A.L. reagent.

* * * * *